United States Patent
Ni et al.

(10) Patent No.: US 9,944,588 B2
(45) Date of Patent: *Apr. 17, 2018

(54) METHOD FOR PREPARING METHYL FORMATE

(71) Applicant: DALIAN INSTITUTE OF CHEMICAL PHYSICS, CHINESE ACADEMY OF SCIENCES, Dalian (CN)

(72) Inventors: Youming Ni, Dalian (CN); Wenliang Zhu, Dalian (CN); Yong Liu, Dalian (CN); Hongchao Liu, Dalian (CN); Zhongmin Liu, Dalian (CN); Lina Li, Dalian (CN); Shiping Liu, Dalian (CN); Hui Zhou, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/526,780

(22) PCT Filed: Nov. 17, 2014

(86) PCT No.: PCT/CN2014/091289
§ 371 (c)(1),
(2) Date: May 15, 2017

(87) PCT Pub. No.: WO2016/077967
PCT Pub. Date: May 26, 2016

(65) Prior Publication Data
US 2017/0320808 A1 Nov. 9, 2017

(51) Int. Cl.
| | | |
|---|---|---|
| *C07C 69/00* | (2006.01) | |
| *C07C 69/06* | (2006.01) | |
| *C07C 67/39* | (2006.01) | |
| *B01D 3/14* | (2006.01) | |
| *B01J 29/70* | (2006.01) | |
| *B01J 29/40* | (2006.01) | |
| *C07C 53/02* | (2006.01) | |
| *C07C 43/10* | (2006.01) | |
| *C07C 43/04* | (2006.01) | |
| *C08F 212/36* | (2006.01) | |
| *C08F 212/08* | (2006.01) | |

(52) U.S. Cl.
CPC .............. *C07C 69/06* (2013.01); *B01D 3/14* (2013.01); *B01J 29/40* (2013.01); *B01J 29/7038* (2013.01); *C07C 67/39* (2013.01); *C07C 43/043* (2013.01); *C07C 43/10* (2013.01); *C07C 53/02* (2013.01); *C08F 212/08* (2013.01); *C08F 212/36* (2013.01)

(58) Field of Classification Search
CPC ......... C07C 69/06; C07C 41/01; C07C 43/04; C07C 43/043; C07C 43/10; C07C 53/02; C07C 67/39; C07C 41/28; C07C 67/00; C07C 67/44; C07C 67/475; B01J 29/7038; B01J 29/40; B01J 31/10; B01J 8/02; B01D 3/14; C08F 212/08; C08F 212/36
See application file for complete search history.

(56) References Cited

U.S. PATENT DOCUMENTS 6,015,875 A * 1/2000 Smith, Jr. ............... C08G 4/00
                                                           203/14
2010/0105947 A1   4/2010 Celik et al.

FOREIGN PATENT DOCUMENTS

| CN | 103254084 A | 8/2013 |
| CN | 104016857 A | 9/2014 |

OTHER PUBLICATIONS

Yan et al., Chemical Industry and Engineering Progress., 29(6), (2010) (English abstract is included).
International Search Report dated Aug. 21, 2015 for related PCT Application No. PCT/CN2014/091289.

* cited by examiner

*Primary Examiner* — Yevgeny Valenrod
*Assistant Examiner* — Blaine G Doletski
(74) *Attorney, Agent, or Firm* — Enshan Hong; VLP Law Group LLP

(57) ABSTRACT

A method for preparing methyl formate in which a raw material containing formaldehyde, methanol and/or dimethyl ether is introduced into a first reaction zone to come into contact with a catalyst A, and a component I is obtained by separation, the component I is introduced into a second reaction zone to come into contact with a catalyst B so as to obtain, by separation, methyl formate as a product, dimethyl ether that is returned to the first reaction zone and a component II that is returned to the second reaction zone, the catalysts have a long service life, the reaction conditions are mild, and the utilization rate of the raw material is high, thus enabling a continuous production for large-scale industrial application.

10 Claims, 1 Drawing Sheet

METHOD FOR PREPARING METHYL FORMATE

RELATED APPLICATIONS

This is a U.S. national stage of international application No. PCT/CN2014/091289 filed on Nov. 17, 2014, the entire content of which is incorporated herein as reference.

TECHNICAL FIELD

The present invention relates to the field of chemistry and chemical industry, and particularly to a method for preparing methyl formate.

BACKGROUND ART

In $C_1$ chemistry, methyl formate has been evolved into a new starting material and structural unit of $C_1$ chemicals for the reasons that it can be produced in a large-scale economically and effectively, and has many downstream products, etc., subsequent to methane chemistry, synthesis gas chemistry, and methanol chemistry. From methyl formate, various $C_1$ chemical products, such as formic acid, acetic acid, ethylene glycol, methyl propionate, methyl acrylate, methyl glycolate, N-formylmorpholine, N-methylformamide, N,N-dimethylformamide, etc., may be produced.

At present, the techniques for synthesizing methyl formate are sensitive to impurities, and have stringent requirements for the purity of raw materials, complicated process routes, high energy consumption, and high investment. In view of the above reasons, the production capacity of a single set is typically not more than 100 thousand tons per year, and thus it is difficult to obtain a scale effect. If methyl formate can be produced with mild conditions and a simple process from inexpensive and easily available bulk chemicals such as formaldehyde, methanol, etc., important economic value will be created.

SUMMARY OF THE INVENTION

According to one aspect of the present application, there is provided a method for preparing methyl formate, comprising at least the steps of:

a) introducing a raw material containing formaldehyde, methanol and/or dimethyl ether into a first reaction zone to come into contact with a catalyst A, so as to obtain a component I;

b) introducing the component I obtained by separation in step a) into a second reaction zone to come into contact with a catalyst B, so as to obtain methyl formate as product, dimethyl ether, and a component II by separation; and c) returning dimethyl ether obtained by separation in step b) to the first reaction zone, and returning the component II to the second reaction zone, wherein in step a), the temperature is 50-100° C. in the first reaction zone; the ratio of formaldehyde, methanol and/or dimethyl ether in the raw material is formaldehyde:methanol and/or dimethyl ether=1:2-4 based on the mole number of carbon atoms contained in respective component; and the mass hourly space velocity of formaldehyde in the raw material is 0.01-15.0 $h^{-1}$;

in step b), the temperature is 50-200° C. and the pressure is 0.1-10 Mpa in the second reaction zone; and the components in the first reaction zone and the second reaction zone are each independently a gas phase and/or a liquid phase.

Preferably, the raw material in step a) is consisted of formaldehyde, methanol and/or dimethyl ether.

The component I mainly contains methylal produced by the reaction in the first reaction zone and dimethyl ether in excess; and the component II mainly contains unreacted methylal in the second reaction zone.

Methylal is produced by the reaction of formaldehyde $CH_2O$, dimethyl ether $CH_3OCH_3$, and methanol $CH_3OH$. Methyl formate $HCOOCH_3$ and dimethyl ether $CH_3OCH_3$ are produced by the disproportionation reaction of methylal $CH_3O—CH_2—OCH_3$. The preparation of methyl formate can be achieved by combining the two-step reactions above with formaldehyde and methanol as raw materials.

The reactions occurred in the first reaction zone include a condensation reaction of formaldehyde and methanol as shown in formula (1) and a condensation reaction of formaldehyde and dimethyl ether as shown in formula (2). The component I contains methylal $CH_3O—CH_2—OCH_3$, which is a product of the condensation reactions above.

$$CH_2O+2CH_3OH=CH_3—CH_2—OCH_3+H_2O \quad \text{formula (1)}$$

$$CH_2O+CH_3OCH_3=CH_3O—CH_2—OCH_3 \quad \text{formula (2)}$$

The reactions occurred in the second reaction zone include a reaction for preparing methyl formate $HCOOCH_3$ and dimethyl ether via a disproportionation reaction of methylal as shown in formula (3):

$$2CH_3O—CH_2—OCH_3=2CH_3OCH_3+HCOOCH_3 \quad \text{formula (3)}$$

According to formula (3), the highest single-pass carbon molar selectivity of methyl formate is theoretically 33.33%.

Dimethyl ether produced in the second reaction zone is returned to the first reaction zone and is subsequently subjected to a condensation reaction with formaldehyde, so as to sufficiently utilize the raw material to obtain more methyl formate. The raw material containing formaldehyde, methanol and/or dimethyl ether means that the raw material contains formaldehyde as well as methanol and/or dimethyl ether. Since dimethyl ether obtained by separation from the second reaction zone is returned to the first reaction zone, the raw material in the first reaction zone contains dimethyl ether. When the returned dimethyl ether is insufficient to maintain the reaction to be performed normally, methanol and/or dimethyl ether is required to be added additionally. Dimethyl ether is returned to the first reaction zone. The overall reaction in the first reaction zone and the second reaction zone is the preparation of methyl formate by formaldehyde coupling. Without consideration of other side reactions and process loss, the raw material of the overall reaction is formaldehyde. With consideration of small amount of process loss and other side reactions, the preparation of methyl formate may be achieved by using formaldehyde and methanol and/or dimethyl ether as the raw material as long as small amount of methanol and/or dimethyl ether is added to the raw material.

$$2CH_2O=HCOOCH_3 \quad \text{formula (4)}$$

The disproportionation reaction of methylal is an endothermic reaction, and there is no risk of temperature runaway. If no other reaction is occurred between the product after reaction and the impurities (such as water) in the raw material, the molar ratio of dimethyl ether produced to methyl formate is 2:1, which is the stoichiometric ratio of the reaction equation. No any byproduct is produced in this reaction and methyl formate is easily separated, methyl formate with relatively high purity can be obtained.

Preferably, the ratio of formaldehyde, methanol and/or dimethyl ether in the raw material is formaldehyde:methanol and/or dimethyl ether=1:2-2.2 based on the mole number of carbon atoms contained in respective component. Further preferably, the ratio of formaldehyde, methanol and/or dimethyl ether in the raw material is formaldehyde:methanol and/or dimethyl ether=1:2 based on the mole number of carbon atoms contained in respective component.

In step a), the process of introducing the raw material into the first reaction zone to come into contact with the catalyst A may be a process wherein the raw material is first come into contact with the catalyst A in a reactor and then is introduced into a separation system for separation; or may be a process wherein both the reaction and the separation are performed in a same unit, namely a catalytic rectification process. In a catalytic rectification unit, the catalyst bed layer is one section or a plurality of sections in a rectification column; meanwhile, it acts as a fixed bed reactor and a column plate/filler of the rectification column, so that an effect of saving the investment of apparatuses can be achieved. The heat of the reaction can be used to supply the heat required by rectification separation, and thus the heat load of the reboiler is reduced and the energy consumption is decreased. The materials are directly separated in the rectification column after reaction, the product exits the rectification system and the unreacted raw material after separation continues to come into contact with the catalyst bed layer for reaction. Therefore, the reaction, the separation, and the returning of the unreacted raw material to the first reaction zone can be achieved simultaneously.

The person skilled in the art is able to adjust the process conditions of the catalytic rectification unit, such as the temperature, pressure, ratio of raw materials, reflux ratio, feeding location, so as to obtain methylal with different purities.

Preferably, in step a), the catalyst A is charged in a rectification unit for reaction; the rectification unit for reaction has a reflux ratio of 0.5-10; the temperature range has an upper limit selected from 90° C. and 100° C., and the temperature range has a lower limit selected from 50° C. and 60° C.; the mass hourly space velocity of formaldehyde in the raw material has an upper limit selected from 3.0 $h^{-1}$ and 15 $h^{-1}$ and a lower limit selected from 0.01 $h^1$ and 0.5 $h^1$. The first reaction zone is consisted of one or more catalytic rectification units. Further preferably, in step a), the catalyst A is charged in a rectification unit for reaction; the rectification unit for reaction has a reflux ratio of 0.5-10 and a temperature of 60-90° C.; the mass hourly space velocity of formaldehyde in the raw material is 0.5-3.0 $h^1$.

Preferably, in step a), the molar ratio of methanol in methanol and/or dimethyl ether in the raw material is 0-50% based on the mole number of carbon atoms contained in respective component. Further preferably, in step a), the range of the molar ratio of methanol in methanol and/or dimethyl ether in the raw material has an upper limit optionally selected from 45%, 40% and 35%, and a lower limit optionally selected from 0%, 5%, 10%, 15% and 20%, based on the mole number of carbon atoms contained in respective component.

Preferably, in step a), dimethyl ether in methanol and/or dimethyl ether in the raw material is partially or entirely derived from the second reaction zone by separation.

Dimethyl ether in methanol and/or dimethyl ether in the raw material may be derived from the second reaction zone by separation, or may be derived from outside the system by addition. If the requirement for the preparation of methylal via the condensation reaction of formaldehyde can be met by returning dimethyl ether obtained by separation from the second reaction zone to the first reaction zone, it is not required to additionally add methanol and/or dimethyl ether. With consideration of possible side reactions and loss in actual production, dimethyl ether obtained by separation from the second reaction zone is returned to the first reaction zone, and it is required to additionally replenish fresh methanol and/or dimethyl ether. Since the reaction performance of methanol is similar to that of dimethyl ether, and methanol has a lower cost than dimethyl ether, as a relatively preferable embodiment, the raw material of the first reaction zone is consisted of fresh formaldehyde, fresh methanol, and dimethyl ether obtained by separation from the second reaction zone.

Preferably, in step a), the catalyst A is optionally selected from one or more of strong acidic cation exchange resins.

Preferably, in step a), the catalyst A is a strong acidic macroporous resin of sulfonated styrene-divinyl benzene copolymer, which is obtained by sulfonating the copolymer of styrene and divinyl benzene with sulfuric acid.

Preferably, in step b), in the second reaction zone, the temperature range has an upper limit optionally selected from 150° C. and 200° C., and a lower limit optionally selected from 50° C. and 60° C.; the pressure range has an upper limit optionally selected from 2 Mpa and 10 Mpa, and a lower limit of 0.1 Mpa. Further preferably, in step b), the temperature is 60-150° C. and the pressure is 0.1-2 MPa in the second reaction zone.

Preferably, in step b), the catalyst B is one or more of an acidic molecular sieve and a strong acidic cation exchange resin.

Preferably, the structural type of the acidic molecular sieve catalyst is MWW, FER, MFI, MOR, FAU, or BEA. Further preferably, the silica-to-alumina ratio Si/Al of the acidic molecular sieve catalyst is 3:1-150:1.

Further preferably, in step b), the catalyst B is selected from one or more of a hydrogen type MCM-22 molecular sieve, a hydrogen type ZSM-5 molecular sieve, a hydrogen type Y zeolite, a hydrogen type Beta molecular sieve, a hydrogen type ferrierite, a hydrogen type zeolite mordenite, and a perfluorosulfonic acid resin (simply referred to as Nafion-H).

According to the common knowledge in the art, a hydrogen type molecular sieve or zeolite is typically obtained via ammonium ion exchange and baking of a molecular sieve or zeolite.

In this application, the second reaction zone is suitable for various forms of reactors, and the person skilled in the art may select different reactors, all of which can achieve the objects and the technical effects of this application. Preferably, the second reaction zone contains one or more of a fixed bed reactor, a tank reactor, a moving bed reactor, and a fluidized bed reactor. Since the catalyst B of the second reaction zone in this application has the advantage of prominently long service life, the use of the fixed bed reactor has relatively great advantages in terms of investment cost, engineering design, and production operation. Therefore, the fixed bed reactor is a relatively preferable embodiment. Further preferably, the second reaction zone is consisted of a fixed bed reactor; or the second reaction zone is consisted of a plurality of fixed bed reactors in parallel and/or in series.

The advantageous effects of this application include, but are not limited to, the following aspects:

1) The method of this application has advantages of low cost, good environment-friendliness, and high production process safety. The raw material is an aqueous formaldehyde solution, a methanol aqueous solution and/or dimethyl ether with a cheap price, and methyl formate with a high-purity can be obtained by a two-step method. The disproportionation reaction of methylal is a simple process with mild reaction conditions, and excellent results of reaction can also be obtained even under a relatively low reaction temperature and pressure. The disproportionation of methylal is an endothermic reaction and there is no risk of temperature runaway, and thus the process safety is high. The catalyst is stable and suitable for large-scale continuous production, the investment and the energy consumption for the separation of products are low, and methyl formate and dimethyl ether are easily obtained with a high-purity. Compared to the process of methanol carbonylation, the use of carbon monoxide as a raw material is avoided, and expensive gas generation units as well as conversion and gas separation units are not required.

2) The catalyst B used in the second reaction zone in the method of this application has the characteristics of long service life and excellent reaction performance.

3) The raw material in the method of this application has a high utilization rate.

4) The method of this application is suitable for not only large-scale integrated production but also small-scale production with low investment in middle and small corporations, and is flexibly applied and rarely limited by regions and supporting facilities.

The present invention has been described in detail above, but the present invention is not limited to specific embodiments described herein. It is to be understood by the person skilled in the art that other modifications and variations can be made without departing from the scope of the invention.

DESCRIPTION OF EMBODIMENTS

Figure 1:
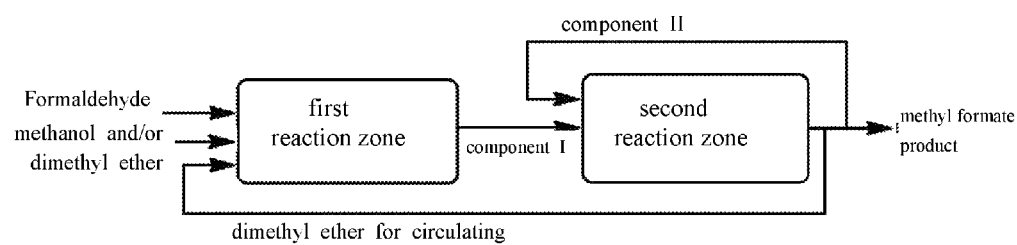
FIG. 1 is a schematic flow chart of a process for synthesizing methyl formate of the present application.

According to an embodiment of the present application, of which the schematic flow chart of the process is shown in FIG. 1, formaldehyde as a raw material and methanol and/or dimethyl ether as a raw material are introduced into a first reaction zone and then separation is performed. The unreacted raw material is in the first reaction zone for further reaction, and a component I (being mainly methylal) obtained by separation is introduced into a second reaction zone. The product of the second reaction zone is separated to obtain dimethyl ether that is returned to the first reaction zone, a component II (being mainly methylal) that is returned to the second reaction zone, and methyl formate that is stored as a product.

The present invention is further elaborated below in conjunction with specific Examples. It is to be understood that these Examples are provided to illustrate this application but are not intended to limit the scope of this application.

Unless specifically stated, raw materials and catalysts in Examples are all commercially purchased, wherein Amberlyst-15 resin is a strong acidic macroporous resin of sulfonated styrene-divinyl benzene copolymer purchased from ROHM HRRS Corporation; DNW resin and D005 resin are strong acidic macroporous resins of sulfonated styrene-divinyl benzene copolymer purchased from Dandong Mingzhu Special Resin Co., Ltd.; D006 resin and D007 resin are strong acidic macroporous resins of sulfonated styrene-divinyl benzene copolymer purchased from Kairui Chemical Co., Ltd.

The analytical methods as well as the calculation of conversion rate and selectivity in Examples are as follows.

An Agilent7890 gas chromatograph provided with an automatic gas sampler, a FID detector, and a PLOT-Q capillary column is used for automatic component analysis of gas/liquid phase components.

In Examples of this application, the single-pass conversion rate of methylal and the single-pass selectivity of methyl formate in the disproportionation reaction are all calculated based on the mole number of carbon.

Conversion rate of methylal=[(the mole number of carbon of methylal in feedstock of the second reaction zone)−(the mole number of carbon of methylal in discharge of the second reaction zone)]÷(the mole number of carbon of methylal in feedstock of the second reaction zone)×(100%)

Selectivity of methyl formate=(the mole number of methyl formate in discharge of the second reaction zone)÷[(the mole number of carbon of methylal in feedstock of the second reaction zone)−(the mole number of carbon of methylal in discharge of the second reaction zone)]×(100%)

The mole number of carbon in this application refers to the mole number of carbon atoms contained in a component.

The present invention will be described in detail below by Examples, but the present invention is not limited to these Examples.

EXAMPLE 1

Figure 2:
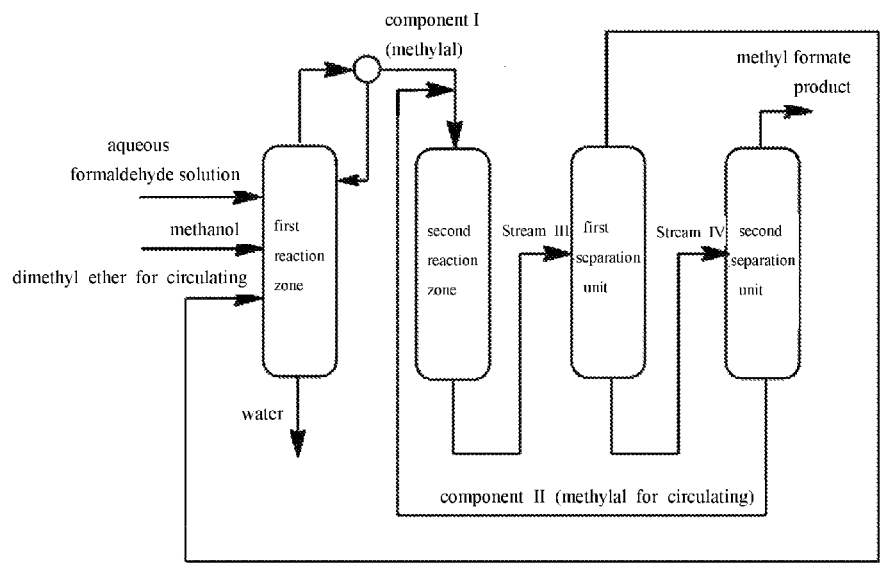
FIG. 2 is a flow chart of a process for synthesizing methyl formate of Example 1.

Reaction Process for the Production of Methyl Formate:

As a typical solution, the reaction process of the method for producing methyl formate of this application was shown in FIG. 2, wherein a catalytic rectification column was used in a first reaction zone for performing the process of preparing methylal by the condensation reaction of formaldehyde, methanol, and dimethyl ether; a fixed bed reactor was used in a second reaction zone for performing the disproportionation reaction of methylal; a primary separation unit was used for the separation of dimethyl ether from the disproportionation reaction products of methylal; and a secondary separation unit was used for the separation of methyl formate from the unreacted raw material in the products of the disproportionation reaction of methylal.

Specifically, the raw material comprised an aqueous formaldehyde solution, methanol, and circulating dimethyl ether obtained from the product by separation. The above-mentioned three streams were introduced into a catalytic rectification column of the first reaction zone. In the rectification column, the unreacted raw material containing formaldehyde, methanol, and dimethyl ether was returned to a catalyst bed layer for further reaction. A component I obtained at the top of the column was mainly methylal as the product of the condensation reaction, and water was obtained at the bottom of the column. The component I was introduced into the second reaction zone for the disproportionation reaction of methylal. A product stream III of the disproportionation reaction was introduced into a first separation unit, and dimethyl ether for circulating and a stream IV were obtained by separation, wherein dimethyl ether for circulating was returned to the first reaction zone and the stream IV was introduced into a second separation unit. A product of methyl formate and a component II were obtained by separation, wherein the component II was mainly methylal for circulating, and the component II was returned to the second reaction zone for further reaction. The production of methyl formate as the product by using formaldehyde and methanol as the raw material can be achieved through the process described above.

The process for preparing methylal via the condensation reaction of formaldehyde, methanol, and dimethyl ether in the first reaction zone was performed according to the following procedure:

In a stainless catalytic rectification column having an inner diameter of 30 mm and a height of 1800 mm, 500 g of an Amberlyst-15 resin catalytic filler having a height of 1200 mm that was packaged by a stainless mesh was loaded as a reaction section at the lower end, a Φ4 mm×4 mm stainless wire having a height of 600 mm was loaded as fillers of a rectification section at the upper end, a condenser having a controllable reflux ratio was provided at the top of the column, a reboiler having a volume of 3000 ml was provided at the bottom of the column, and a heating wire was wound on the outer wall of the reaction section to allow the temperature sequentially from top to bottom to be uniformly increased from 60° C. to 90° C. A 37% aqueous formaldehyde solution, a 96% aqueous methanol solution, and dimethyl ether were sequentially introduced to three feeding ports from top to bottom of the catalytic rectification column, and the ratio between these three materials was shown in Table 1. The power and the reflux ratio of the reboiler was gradually adjusted, until methylal with a purity higher than 99.5% can be obtained from the top of the column (in subsequent Examples, when formaldehyde:methanol and/or dimethyl ether was less than 1:2, i.e., when methanol and/or dimethyl ether was in excess according to the stoichiometric ratio, the component I may contain excessive dimethyl ether, and the excessive dimethyl ether was not counted in the concentration of methylal at this point).

The preparation of methyl formate by the disproportionation reaction of methylal in the second reaction zone was performed according to the following procedure:

300 g of an hydrogen type MCM-22 molecular sieve catalyst having a silica-to-alumina ratio (Si:Al)=40:1 was baked under air atmosphere in a muffle furnace at 550° C. for 5 hours, tablet-compressed, pulverized, and sieved to 20-40 mesh. 200 g of a sample of this acidic MCM-22 molecular sieve catalyst was weighed and charged into a stainless reaction tube having an inner diameter of 30 mm, and then was activated with nitrogen gas under normal pressure at 550° C. for 4 hours. The reaction temperature was then reduced to 90° C. Methylal is obtained from the first reaction zone by separation under a reaction pressure of 0.1 MPa. The product was analyzed through gas chromatography, and the single-pass selectivity of methylal and the single-pass selectivity of methyl formate were calculated. The results of the reaction can be seen in Table 1. The product obtained in the second step of the reaction was subjected to two-stage rectification separation to obtain methyl formate, dimethyl ether, and unreacted methylal, wherein the component of methyl formate was stored as a product; dimethyl ether was returned to the first reaction zone, and the unreacted methylal was returned to the second reaction zone.

By combining the first step and the second step of the reaction, a 37% aqueous formaldehyde solution and a 96% aqueous methanol solution may be used as the raw material to produce methyl formate with a purity of 99.99% or more.

EXAMPLES 2-6

The catalyst A in the first reaction zone, the catalyst B in the second reaction zone, the feeding ratio of materials in the first zone, the mass hourly space velocity of formaldehyde in feedstock of the first zone, the temperature of the second reaction zone, the pressure of the second reaction zone were shown in Table 1 respectively, and other operation steps were all the same as those in Example 1. The results of the reaction can be seen in Table 1.

EXAMPLES 7-8

The catalyst B of the second reaction zone can be seen in Table 1. 200 g of a 20-40 mesh catalyst was weighed and charged in a stainless reaction tube having an inner diameter of 30 mm, and was activated with nitrogen gas under normal pressure at 100° C. for 1 hours. A reaction was then performed. The catalyst A in the first reaction zone, the feeding ratio of materials in the first zone, the mass hourly space velocity of formaldehyde in feedstock of the first zone, the temperature of the second reaction zone, the pressure of the second reaction zone were shown in Table 1 respectively, and other operation steps were all the same as those in Example 1. The results of the reaction can be seen in Table 1.

EXAMPLE 9

The second reaction zone was in a form of two fixed bed reactors connected in series, each of the reactors was loaded with 100 g of a catalyst, and other reaction conditions can be seen in Table 1. Other operations were the same as those in Example 7. The results of the reaction can be seen in Table 1.

EXAMPLE 10

The second reaction zone was in a form of two fixed bed reactors connected in parallel, each of the reactors was loaded with 100 g of a catalyst, and other reaction conditions can be seen in Table 1. Other operations were the same as those in Example 7. The results of the reaction can be seen in Table 1.

TABLE 1

| | | | | |
|---|---|---|---|---|
| | | | Reaction conditions and results of Examples 1-10 | |
| Examples | Catalyst A in the first reaction zone | Catalyst B in the second reaction zone | Molar ratio of carbon in feedstock of the first reaction zone (formaldehyde:methanol:dimethyl ether) | mass hourly space velocity of formaldehyde in feedstock of the first reaction zone (h$^{-1}$) |
| 1 | Amberlyst-15 resin | Hydrogen type MCM-22 (Si/Al = 40) | 1:0.2:1.8 | 3.0 |
| 2 | Amberlyst-15 | Hydrogen type | 1:0.4:1.7 | 0.5 |

TABLE 1-continued

Reaction conditions and results of Examples 1-10

|   |   |   |   |   |
|---|---|---|---|---|
|   | resin | ferrierite (Si/Al = 10) |   |   |
| 3 | DNW resin | Hydrogen type ZSM-5 (Si/Al = 150) | 1:1:1 | 0.01 |
| 4 | D005 resin | Hydrogen type zeolite mordenite (Si/Al = 3/1) | 1:0:3 | 15 |
| 5 | D006 resin | Hydrogen type Y (Si/Al = 20) | 1:0:2.2 | 6 |
| 6 | D007 resin | Hydrogen type Beta (Si/Al = 15) | 1:0:4 | 1.5 |
| 7 | Amberlyst-15 resin | Nafion-H resin | 1:0.2:1.8 | 1.0 |
| 8 | Amberlyst-15 resin | Amberlyst-15 resin | 1:0.2:1.8 | 1.0 |
| 9 | Amberlyst-15 resin | Nafion-H resin | 1:0.2:1.8 | 1.0 |
| 10 | Amberlyst-15 resin | Nafion-H resin | 1:0.2:1.8 | 1.0 |

| Examples | Temperature of the second reaction zone (° C.) | Pressure of the second reaction zone (MPa) | Single-pass conversion rate of methylal (%) | Single-pass selectivity of methyl formate (%) | Single-pass service life of the catalyst in the second reaction zone (day) |
|---|---|---|---|---|---|
| 1 | 90 | 0.1 | 80.8 | 33.1 | 140 |
| 2 | 150 | 2 | 95.5 | 33.2 | 150 |
| 3 | 60 | 1 | 40.2 | 33.0 | 310 |
| 4 | 200 | 10 | 70.2 | 33.1 | 105 |
| 5 | 50 | 5 | 36.5 | 33.2 | 145 |
| 6 | 120 | 0.5 | 80.1 | 33.3 | 180 |
| 7 | 100 | 0.3 | 77.5 | 33.1 | 200 |
| 8 | 100 | 0.3 | 42.3 | 33.2 | 210 |
| 9 | 100 | 0.3 | 76.3 | 33.1 | 205 |
| 10 | 100 | 0.3 | 72.5 | 33.1 | 220 |

Note 1:
Amberlyst-15 was purchased from ROHM HRRS Corporation; DNW and D005 were purchased from Dandong Mingzhu Special Resin Co., Ltd.; D006 and D007 were purchased from Kairui Chemical Co., Ltd.; and Nafion-H was purchased from DuPont Corporation, US.
Note 2:
All the condition parameters in Table 1 were data at steady state.

The above contents are only several Examples of this application and do not limit this application in the form. Although preferred Examples are used to disclose this application as above, they are not intended to limit this application. Without departing from the scope of the technical solution of this application, some variations and modifications made by any person skilled in the art using the technique contents disclosed above are all equivalent to equivalent Examples and are all within the scope of the technical solution.

What is claimed is:

1. A method for preparing methyl formate, comprising at least the steps of:
   a) introducing a raw material containing formaldehyde, methanol and/or dimethyl ether into a first reaction zone to come into contact with a catalyst A, so as to obtain a component I;
   b) introducing the component I obtained by separation in step a) into a second reaction zone to come into contact with a catalyst B, so as to obtain methyl formate as a product, dimethyl ether, and a component II by separation; and
   c) returning dimethyl ether obtained in step b) to the first reaction zone, and returning the component II to the second reaction zone;
   wherein, in step a), the temperature is 50-100° C. in the first reaction zone; the ratio of formaldehyde, methanol and/or dimethyl ether in the raw material is formaldehyde:methanol and/or dimethyl ether=1:2-4 based on the mole number of carbon atoms contained in respective component; and the mass hourly space velocity of formaldehyde in the raw material is 0.01-15.0 h−1;
   in step b), the temperature is 50-200° C. and the pressure is 0.1-10 Mpa in the second reaction zone; and
   the components in the first reaction zone and the second reaction zone are each independently a gas phase and/or a liquid phase.

2. The method according to claim 1, wherein in step a), the catalyst A is charged in a rectification unit for reaction; the rectification unit for reaction has a reflux ratio of 0.5-10 and a temperature of 60-90° C.; and the mass hourly space velocity of formaldehyde in the raw material is 0.5-3.0 h−1.

3. The method according to claim 1, wherein in step a), the molar ratio of methanol and/or methanol in dimethyl ether in the raw material is 0-50% based on the mole number of carbon atoms contained in respective component.

4. The method according to claim 1, wherein in step a), dimethyl ether in methanol and/or dimethyl ether in the raw material is partially or entirely obtained from the second reaction zone by separation.

5. The method according to claim 1, wherein in step a), the catalyst A is a strong acidic cation exchange resin.

6. The method according to claim 1, wherein in step a), the catalyst A is a strong acidic macroporous resin of sulfonated styrene-divinyl benzene copolymer.

7. The method according to claim 1, wherein in step b), the temperature is 60-150° C. and the pressure is 0.1-2 MPa in the second reaction zone.

8. The method according to claim 1, wherein in step b), the catalyst B is one or more of an acidic molecular sieve and a strong acidic cation exchange resin.

9. The method according to claim 1, wherein in step b), the catalyst B is selected from one or more of a hydrogen type MCM-22 molecular sieve, a hydrogen type ZSM-5 molecular sieve, a hydrogen type Y zeolite, a hydrogen type Beta molecular sieve, a hydrogen type ferrierite, a hydrogen type zeolite mordenite, and a perfluorosulfonic acid resin.

10. The method according to claim 1, wherein the second reaction zone is consisted of a fixed bed reactor; or the second reaction zone is consisted of a plurality of fixed bed reactors in parallel and/or in series.

* * * * *